(12) United States Patent
Griego et al.

(10) Patent No.: US 6,663,596 B2
(45) Date of Patent: Dec. 16, 2003

(54) DELIVERING MATERIAL TO A PATIENT

(75) Inventors: John A. Griego, Blackstone, MA (US); Marcia Buiser, Brighton, MA (US); Carla M. Wiese, Newton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/928,779

(22) Filed: Aug. 13, 2001

(65) Prior Publication Data

US 2003/0032937 A1 Feb. 13, 2003

(51) Int. Cl.[7] .............................................. A61M 5/178
(52) U.S. Cl. ............................ 604/164.02; 604/164.01; 604/284
(58) Field of Search ....................... 604/164.02, 164.01, 604/164.11, 167.01, 167.03, 167.04, 30, 31, 34, 82, 83, 93.01, 523, 533, 534, 284, 264

(56) References Cited

U.S. PATENT DOCUMENTS

| | | |
|---|---|---|
| 4,270,535 A | 6/1981 | Bogue et al. |
| 4,950,238 A | 8/1990 | Sullivan |
| 5,037,431 A | 8/1991 | Summers et al. |
| 5,084,013 A | 1/1992 | Takase |
| 5,122,113 A | 6/1992 | Hattler |
| 5,135,482 A | 8/1992 | Neracher |
| 5,156,592 A | 10/1992 | Martin et al. |
| 5,188,593 A | 2/1993 | Martin |
| 5,211,627 A | 5/1993 | William |
| 5,219,326 A | 6/1993 | Hattler |
| 5,219,335 A | 6/1993 | Willard et al. |
| 5,242,387 A | 9/1993 | Loughlin |
| 5,249,580 A | 10/1993 | Griffith |
| 5,271,743 A | 12/1993 | Hattler |
| 5,370,610 A | 12/1994 | Reynolds |
| 5,376,069 A | 12/1994 | Hattler |
| 5,453,088 A | 9/1995 | Boudewijn et al. |
| 5,458,584 A | 10/1995 | Ginn et al. |
| 5,484,604 A | 1/1996 | Solomon et al. |
| 5,490,611 A | 2/1996 | Bernosky et al. |
| 5,501,663 A | 3/1996 | Hattler et al. |
| 5,505,263 A | 4/1996 | White et al. |
| 5,549,569 A | 8/1996 | Lynn et al. |
| 5,596,084 A | 1/1997 | Sanderson et al. |
| 5,624,395 A | 4/1997 | Mikhail et al. |
| 5,711,917 A | 1/1998 | Juranas et al. |

(List continued on next page.)

FOREIGN PATENT DOCUMENTS

| | | |
|---|---|---|
| EP | 0308768 A2 | 3/1989 |
| EP | 0324365 A2 | 7/1989 |
| EP | 0343910 A2 | 11/1989 |
| EP | 0421031 A1 | 4/1991 |
| EP | 0442535 A1 | 8/1991 |
| EP | 0486157 A2 | 5/1992 |
| EP | 0486720 A1 | 5/1992 |
| EP | 0521376 A2 | 1/1993 |
| EP | 0575065 A1 | 12/1993 |
| EP | 0592802 A1 | 4/1994 |

(List continued on next page.)

OTHER PUBLICATIONS

PCT International Search Report, PCT/US 02/25020.

*Primary Examiner*—Long V. Le
*Assistant Examiner*—Ann Y Lam
(74) *Attorney, Agent, or Firm*—Testa, Hurwitz & Thibeault, LLP

(57) ABSTRACT

A delivery catheter for delivering material(s) into the body of a mammal can include a first elongated member and a second elongated member. At least a portion of the second elongated member can be slidably disposed within a lumen of the first elongated member. The delivery catheter can mix two materials and then introduce the mixed materials into the body of a mammal.

22 Claims, 8 Drawing Sheets

U.S. PATENT DOCUMENTS

| | | | |
|---|---|---|---|
| 5,800,411 A | * | 9/1998 | Nakada et al. ............... 604/280 |
| 5,843,022 A | | 12/1998 | Willard et al. |
| 5,874,100 A | | 2/1999 | Mahoney et al. |
| 5,887,755 A | | 3/1999 | Hood, III |
| 5,986,164 A | | 11/1999 | Kershaw et al. |
| 6,114,594 A | | 9/2000 | Barikosky |
| 6,146,373 A | | 11/2000 | Cragg et al. |

FOREIGN PATENT DOCUMENTS

| | | |
|---|---|---|
| EP | 0786233 A1 | 7/1997 |
| EP | 0798010 A1 | 10/1997 |
| EP | 0798026 A1 | 10/1997 |
| EP | 0864633 A2 | 9/1998 |
| EP | 0875285 A1 | 11/1998 |
| EP | 0884507 A1 | 12/1998 |
| EP | 0916396 A2 | 5/1999 |
| EP | 0971165 A2 | 1/2000 |
| EP | 0972564 A2 | 1/2000 |
| EP | 1072282 A1 | 1/2001 |
| EP | 1073167 A2 | 1/2001 |
| WO | 9911191 | 3/1999 |
| WO | 0018469 | 4/2000 |

* cited by examiner

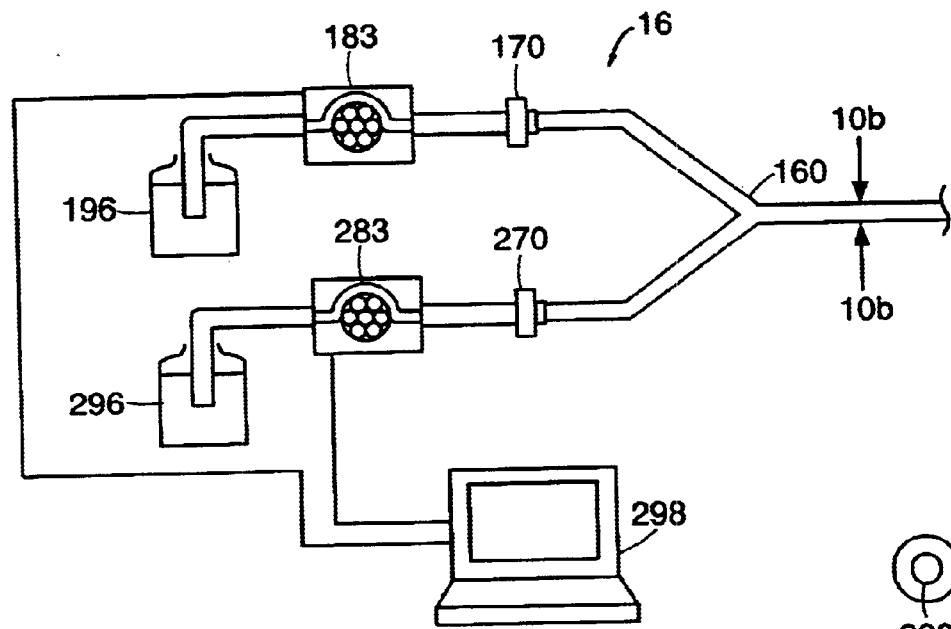
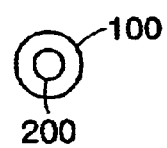
FIG. 10a
FIG. 10b
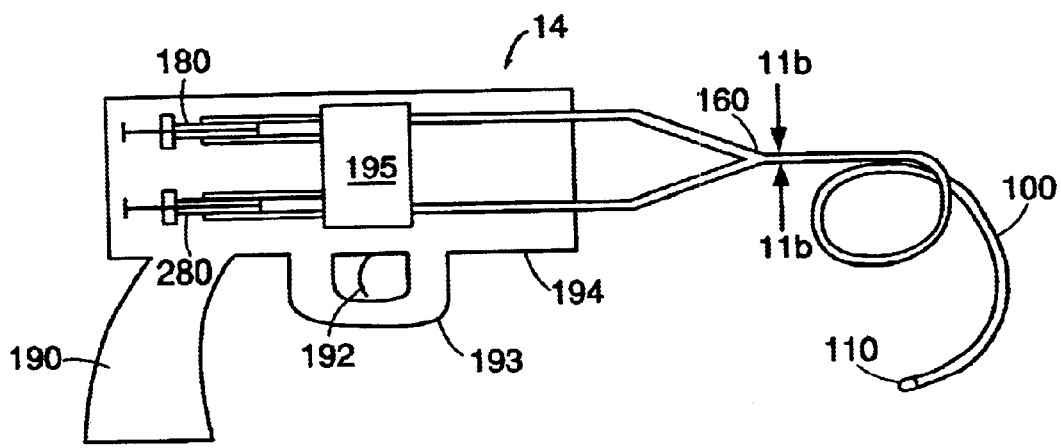
FIG. 11a
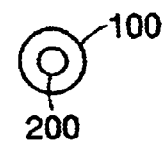
FIG. 11b
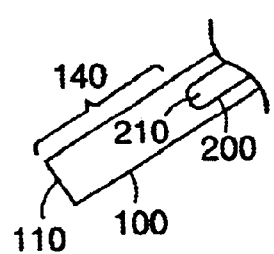
FIG. 11c

DELIVERING MATERIAL TO A PATIENT

TECHNICAL FIELD

This invention generally relates to medical devices and methods for delivering material(s) to a patient.

BACKGROUND INFORMATION

Medical conditions sometimes require the replacement or support of a damaged tissue or structure. Such replacement or support can be made via the use of fillers, either temporarily or permanently. Exemplary applications of such filler compositions include sutures and surgical nets that have been used for organ support in spleen, liver, and kidney repair procedures. A non-immunogenic, bioerodible, implantable composition with alginate fibers is known, as is a biological tissue transplant coated with a stabilized multi-layer alginate. Transplantable artificial pancreatic tissue can be prepared from an alginic acid gel precursor, a matrix monomer, and pancreas cells with $Ca^{2+}$ ions and a matrix monomer polymerization catalyst. The calciumalginic acid composition is used to provide mechanical integrity to the mixture while the matrix monomer is polymerized, after which the calcium-alginic acid composition is removed to leave a porous matrix. The calcium-alginic acid composition functions as a processing aid not as a structural member in the final artificial device. Also, alginate fibers have been used in preparation of wound dressings.

Formation of fibers with ionically crosslinked alginates requires contacting crosslinking agents, such as the cation of choice, with the alginate of choice. While contacting a crosslinking agent with an alginate generally is not considered difficult, controlling the formation and termination of the alginate fibers has been difficult. The difficulty arises from the rapidity in which alginate crosslinks once exposed to crosslinking ions. Controlling fiber formation and fiber termination is a major problem of existing preparation methods that employ the simple mixing of the two agents.

SUMMARY OF THE INVENTION

Because of the rapid rate of crosslinking, an alginate and a crosslinking agent generally should be separately delivered to, and crosslinked at, the location in need of alginate fibers. Such in situ formation provides maximum effectiveness in generating alginate fibers with the desired shape and size at the desired location. Introduction and/or relocation of formed alginate fibers generally is not effective or efficient.

One object of the invention involves mixing, delivering, and terminating delivery of a crosslinking agent and a crosslinkable polymer at the location of need, thereby providing efficient delivery of fibrous material and minimizing potential for complications.

In one aspect, the invention relates to a delivery catheter. The delivery catheter can include a first elongated member and a second elongated member. The first elongated member defines a first distal opening, a first lumen extending within the first elongated member, and a distal section of the first lumen near the first distal opening. The first elongated member delivers a first material through the first lumen and into the distal section of the first lumen. The second elongated member includes a distal valve and defines a second lumen extending within the second elongated member. The second elongated member is designed for delivering a second material through the second lumen and the distal valve into the distal section of the first lumen. At least a portion of the second elongated member is slidably disposed within at least a portion of the first lumen such that the distal valve is selectively slidable (i) to allow delivery of the second material through the second lumen, the distal valve, and into the distal section of the first lumen, and (ii) to push at least some of the first and second materials from the distal section of the first lumen out of the first distal opening.

In one embodiment of the invention, the delivery catheter comprises a one-way flowcontrol distal valve such as a slit in the wall of the inner elongated member that opens and closes upon pressure differential. In another embodiment, the delivery catheter further contains an access joint for insertion of at least a portion of the second elongated member into a portion of the first lumen. In yet another embodiment, the delivery catheter further contains a first and second pumps connected to the first and second elongated members. Each of the pumps may further contain an injector. In yet another embodiment, the delivery catheter comprises a stabilizing structure (e.g. spokes) to stabilize the second elongated member so that it is substantially coaxial to the first elongated member. In yet another embodiment, the first elongated member of the catheter is transmutable such that the distal valve is locatable outside the first lumen and outside the first distal opening.

In another aspect, the invention relates to a method for delivering an extrudable material within the body of a mammal. The method includes the following steps. A delivery catheter as described above is provided to deliver a first and second materials into a body. A fibrous material is extruded out of the distal section and into the body of a mammal. In one embodiment, the extrusion step includes delivering through the first lumen to the distal section a first material having a crosslinking agent and delivering through the second lumen to the distal section a second material having a crosslinkable polymer. In one embodiment, the first material surrounds the second material as both materials are introduced into the distal section of the first lumen. The contacting of the first material with the second material results in the formation of crosslinked polymeric material and the generation of a fiber inside the distal section. The sustained delivery of the first and second materials into the distal section forces the fiber to be extruded out of the distal section into a body when the catheter is positioned within a body of a patient. The formation of the crosslinked polymeric material may be stopped by terminating the feed of either or both of the first and second materials into the distal section. The method may further include cutting the crosslinked polymeric material so formed. To cut the polymeric material, introduction of one or both of the first and second materials can be terminated. The crosslinked polymeric material can be cut by the distal valve. To facilitate its exit, the crosslinked polymeric material can be pushed by a pressure exerted from the distal valve and/or by the pressure exerted from the sustained delivery solely of the first material into and out of the distal section.

The foregoing and other aspects, features, embodiments, and advantages of the invention will become apparent from the following description, figures, and claims.

BRIEF DESCRIPTION OF THE DRAWINGS

The drawings are not necessarily to scale, emphasis instead generally being placed upon illustrating the principles of the invention.

FIG. 10a is a schematic view of a possible embodiment of a delivery system according to the invention.

FIG. 10b is a transversal cross-sectional view of a distal portion of the delivery system shown in FIG. 10a, illustrating the positioning of the first and second elongated members.

FIG. 11a is a schematic view of an embodiment of a delivery catheter according to the invention, illustrating an embodiment of a gun-like delivery system according to the invention.

FIG. 11b is a transversal cross-sectional view of a distal portion of the delivery system shown in FIG. 10a, illustrating the positioning of the first and second elongated members.

FIG. 11c is a longitudinal cross-sectional view of a distal portion of the delivery system shown in FIG. 10a, illustrating the distal section of the first lumen.

DESCRIPTION

Figure 1:
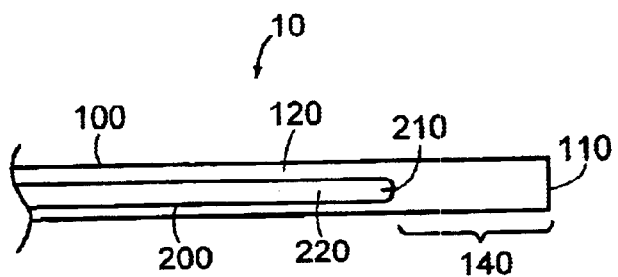
FIG. 1 is a cross-sectional schematic view of a distal portion of one possible embodiment of a delivery catheter according to the invention.

The invention generally relates to delivery catheters and related methods for delivering and mixing agents within the body of a patient. Referring to FIG. 1, in one embodiment, a delivery catheter 10 includes a first elongated member 100 and a second elongated member 200. The first elongated member 100 defines a first distal opening 110 and a first lumen 120 extending within the first elongated member 100. The first elongated member 100 conveys a first material through the first lumen 120 and into a distal section 140 of the first lumen 120 near the first distal opening 110. The second elongated member 200 includes a distal valve 210 and a second lumen 220 extending within the second elongated member 200. The second elongated member 200 conveys a second material through the second lumen 220 and the distal valve 210 and into the distal section 140. At least a portion of the second elongated member 200 is slidably disposed within at least a portion of the first lumen 100 such that the distal valve 210 is selectively slidable (i) to allow delivery of the second material through both the second lumen 220 and the distal valve 210 and into the distal section 140, and (ii) to push at least some of the first and second materials and the fiber resulting from their mixing from the distal section 140 and out of the first distal opening 110.

The distal valve 210 may be a flow-control valve placed at the distal end of the second elongated member 200. The distal valve may be used to control the flow of the first and second materials and the formation of fibers resulting from crosslinking of the second material (such as an alginate solution) with the first material (such as a calcium chloride solution).

Figure 2A:
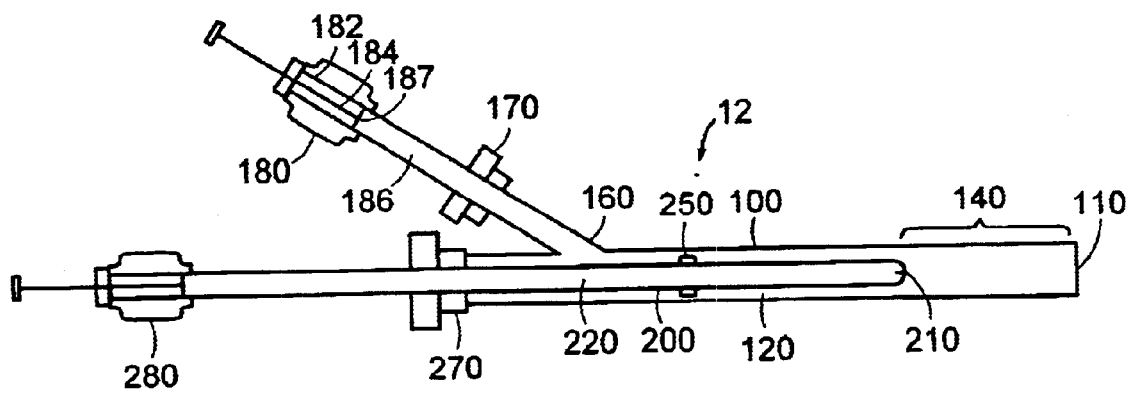
FIG. 2a is a partial cross-sectional schematic view of an embodiment of an entire delivery catheter according to the invention.

Now referring to FIG. 2a, the delivery catheter 12 further includes a Y-shaped access joint or seal 160 which permits access by the distal end of elongated member 200 to the first lumen 120. In addition, the delivery catheter 12 includes a first injector 180, a second injector 280, and connection ports or seals 170 and 270 which connect injectors 180 and 280 with the first and second elongated members 100 and 200, respectively. The first and second injectors 180 and 280 are used for delivering agents to the distal section 140 through the first and second elongated members 100 and 200.

Figure 2B:
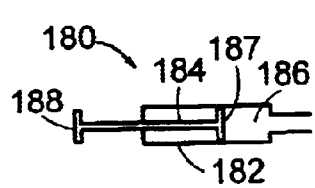
FIG. 2b is a cross-sectional view of a possible embodiment of an injector of the delivery catheter according to the invention.
Figure 2C:
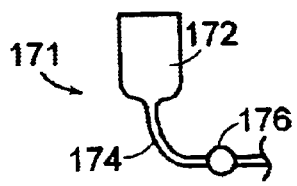
FIG. 2c is a cross-sectional view of a possible embodiment of an injector of the delivery catheter according to the invention.

Any device may be used as an injector as long as the desired purpose is achieved. For example, the injector may be a syringe as shown in FIG. 2b. The syringe includes tubular walls 182 which define a syringe reservoir 186, a shaft 184, a handle 188, and a seal 187. Alternatively as shown in FIG. 2c, an injector 171 includes a reservoir 172 connected to the rest of the delivery catheter 12 through a tube 174 and a valve 176 to control fluid flow. The rate of flow can also be adjusted by changing the height of the reservoir 172 relative to the valve 176. Injectors may incorporate measurement grades thereon to measure the amount of delivery from each injector.

Figure 3:
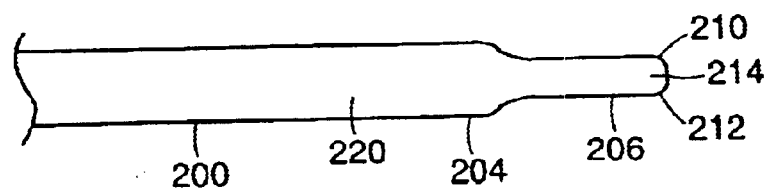
FIG. 3 is a cross-sectional schematic view of the second elongated member of one possible embodiment of a delivery catheter according to the invention.

The second elongated member 200 may have a constant outer diameter throughout its length or it may have a narrowing or widening portion. Referring to FIG. 3, one embodiment of the second elongated member 200 of the delivery catheter includes a wider proximal portion 204 and a narrower distal portion 206. A distal valve 210 is located in the distal portion 206 of the second elongated member 200. The second elongated member 200 defines a lumen or passageway 220. The distal valve 210 may be a one-way flow-control valve designed to allow liquid or gel to flow out of the second lumen 220 through the distal valve 210 but not back into the second lumen 220. The distal valve 210 may also be a two-way flow control valve if the application so requires.

The distal valve 210 may include a deformable slit 214 cut in the walls 212 forming the distal end of the second elongated member 200. The distal valve 210 operates by a deformation of the walls 212 adjoining the slit 214 upon application of greater pressure in the second lumen 220 than in the distal section 140. This pressure differential may be applied either by increasing pressure in the second lumen 220 or by decreasing pressure in the distal section 140. Upon a pressure differential, portions of the walls 212 of the distal valve 210 move distally and radially outwards raising the top lip and/or lowering the lower lip of the slit 214 and thus creating an opening. Upon a negative pressure differential, the walls 212 of the distal valve 210 press the top lip downwards and/or the bottom lip upwards until the lips abut one another. This abutting of the lips and the curvature and strength of the walls 212 in distal valve 210 prevent the walls 212 from collapsing inwards and thus resist the negative pressure differential from reopening the valve and liquid to flow in the opposite direction, back into the second lumen 220. Thus, operation of the distal valve 210 may be controlled by varying the pressure inside the second lumen 220. The deformable slit can be of many shapes and sizes depending on the applications. Illustrative examples are shown in FIGS. 4a–d, 5a–d, 6a–d, and 7a–d.

Figure 4A:
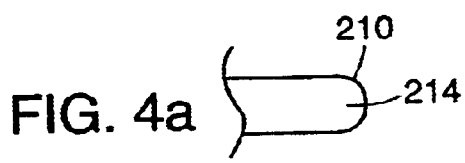
FIG. 4a shows a schematic front view of a closed deformable flow-control valve of one possible embodiment of a delivery catheter according to the invention.
Figure 4B:
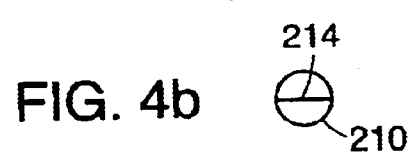
FIG. 4b shows a schematic side view of a closed deformable flow-control valve of one possible embodiment of a delivery catheter according to the invention.
Figure 4C:
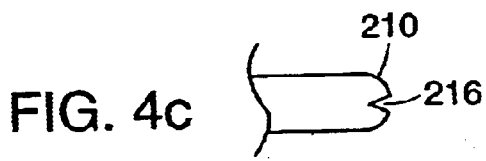
FIG. 4c shows a schematic front view of an opened deformable flow-control valve of one possible embodiment of a delivery catheter according to the invention.
Figure 4D:
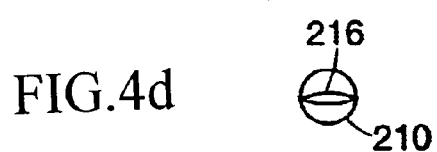
FIG. 4d shows a schematic side view of an opened deformable flow-control valve of one possible embodiment of a delivery catheter according to the invention.
Figure 5A:
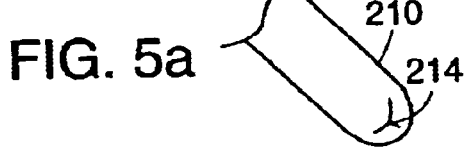
FIG. 5a shows a schematic perspective view of a closed deformable flow-control valve of one possible embodiment of a delivery catheter according to the invention.
Figure 5B:
FIG. 5b shows a schematic side view of a closed deformable flow-control valve of one possible embodiment of a delivery catheter according to the invention.
Figure 5C:
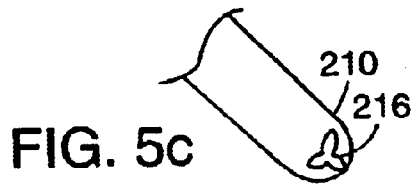
FIG. 5c shows a schematic perspective view of an opened deformable flow-control valve of one possible embodiment of a delivery catheter according to the invention.
Figure 5D:
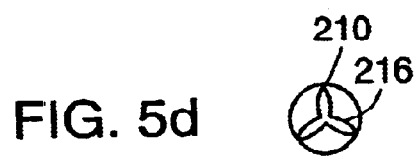
FIG. 5d shows a schematic side view of an opened deformable flow-control valve of one possible embodiment of a delivery catheter according to the invention.
Figure 6A:
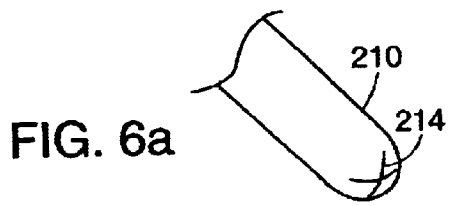
FIG. 6a shows a schematic perspective view of a closed deformable flow-control valve of one possible embodiment of a delivery catheter according to the invention.
Figure 6C:
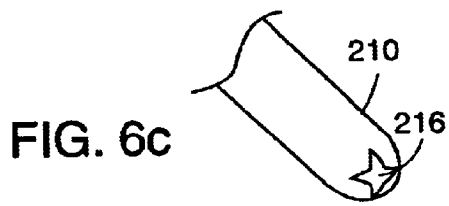
FIG. 6c shows a schematic perspective view of an opened deformable flow-control valve of one possible embodiment of a delivery catheter according to the invention.
Figure 6B:
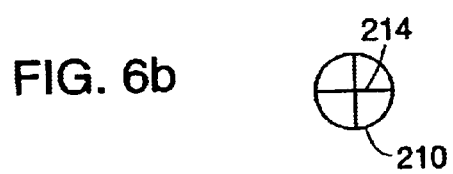
FIG. 6b shows a schematic side view of a closed deformable flow-control valve of one possible embodiment of a delivery catheter according to the invention.
Figure 6D:
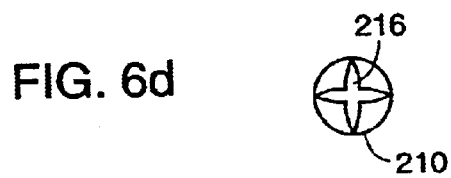
FIG. 6d shows a schematic side view of an opened deformable flow-control valve of one possible embodiment of a delivery catheter according to the invention.
Figure 7A:
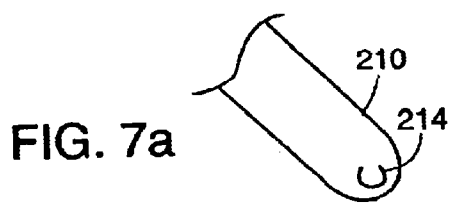
FIG. 7a shows a schematic perspective view of a closed deformable flow-control valve of one possible embodiment of a delivery catheter according to the invention.
Figure 7C:
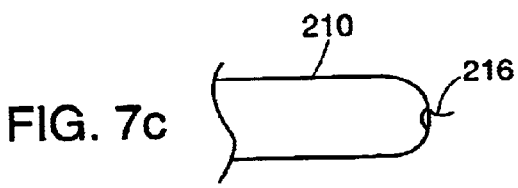
FIG. 7c shows a schematic front view of an opened deformable flow-control valve of one possible embodiment of a delivery catheter according to the invention.
Figure 7B:
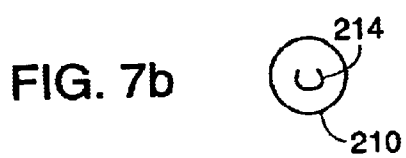
FIG. 7b shows a schematic side view of a closed deformable flow-control valve of one possible embodiment of a delivery catheter according to the invention.
Figure 7D:
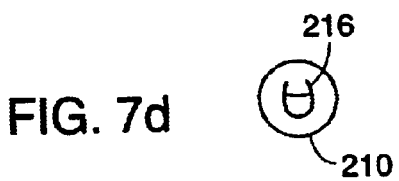
FIG. 7d shows a schematic side view of an opened deformable flow-control valve of one possible embodiment of a delivery catheter according to the invention.

FIGS. 4a–b show one embodiment of the distal valve having a transversal slit 214 in a closed configuration. The deformable slit 214 is a linear cut in a rounded tip of the second elongated member 200. When open (FIGS. 4c–d) the lips of distal valve defines an eye-shape opening 216. Depending on the flexibility of the material forming the second elongated member, the opening geometry may vary from a three-legged star to a triangle or a four-legged star to a square, for examples. In FIGS. 5a–b, the deformable slit 214 has three arms of equal length separated by three pie-shape walls (three 120° angles). Upon positive pressure differential, the three walls deform distally to form a three-legged star opening 216 (FIGS. 5c–d). In FIGS. 6a–b, the deformable slit 214 and the corresponding opening 216 have four arms of equal length separated by four pie-shape walls (four 90° angles). Upon positive pressure differential, the four walls deform distally to form a four-legged star opening 216 (FIGS. 6c–d). In FIGS. 7a–b, the deformable slit 214 is "C"-shaped walls that opens to form a "D"-shaped opening 216 (FIGS. 7c-d).

When open, the slit openings can have an area from about 0.00001 mm$^2$ to about 100 mm$^2$ depending on the applications and the desired cross-section size of the resulting fibers. For example, maximum opening area may range from about 0.00001 mm$^2$ to about 0.0001 mm$^2$, from about 0.0001 mm$^2$ to about 0.001 mm$^2$, from about 0.001 mm$^2$ to about 0.01 mm$^2$, from about 0.01 mm$^2$ to about 0.1 mm$^2$, from about 0.1 mm$^2$ to about 1 mm$^2$, from about 1 mm$^2$ to about 10 mm$^2$, and from about 10 mm$^2$ to about 100 mm$^2$. The distal valve 210 may be a built-in feature at the distal end of the distal portion 206 of the second elongated member 200. Thus, in one embodiment, the deformable slit 214 is created on the distal tip of the second elongated member 200. Alternatively, the distal valve 210 may be a separate device attached (such as by screwing or direct bonding) to the distal end of the distal portion 206 of second elongated member 200. In either embodiment, the material composition for the distal valve 210 may be the same or different from that of the rest of the second elongated member 200. In the later case, for example, the distal valve 210 may be made of a metallic material while the second elongated member 200 is made of a plastic material.

The shape, size, and material composition of various components of the delivery catheter, including the first elongated member 100, the second elongated member 200 with the distal valve 210, may be selected according to the need of the application. The first elongated member 100 and the second elongated member 200 may be made with flexible materials if flexibility is required to access the body cavity into which to introduce the fibers. For example, long, thin, and flexible elongated members may be preferred when the device is to be used for delivery of fibers deep inside the body or within the vasculature such as to fill an aneurysm. Short and more rigid elongated members may be used for sub-topical applications such as tissue bulking of the lips or urethral sphincters, for example. Overall, the length of the first elongated member 100 and the second elongated member 200 may range from about 1 centimeter to any length required to accomplish the goal at hand, for example, about 3 meters. Illustrative ranges of length of the elongated members 100 and 200 include from about 1 centimeter to about 5 centimeters, from about 5 centimeters to about 0.5 meter, from about 0.5 meter to about 1 meter, and from about 1 meter to about 3 meters. The diameter of the first elongated member 100 and the second elongated member 200 may range from about 0.001 millimeter to about 20 millimeters, again depending on the application at hand. Illustrative ranges of the diameter of the elongated members 100 and 200 include about 0.001 millimeter to about 0.01 millimeter, from about 0.01 millimeter to about 0.1 millimeter, from about 0.1 millimeter to about 1 millimeter, from about 1 millimeter to about 5 millimeters, and from about 5 millimeters to about 20 millimeters. The second elongated member 200 may also include one or more legs on its periphery to maintain its position within the first lumen 120. These legs may be positioned at the distal end of catheter 200 or along a segment near the distal end. Alternatively, if the material to be delivered in the first lumen 120 is sufficiently viscous or the pressure and flow is sufficiently elevated the position may be maintained without requiring such peripheral structures.

Figure 8A:
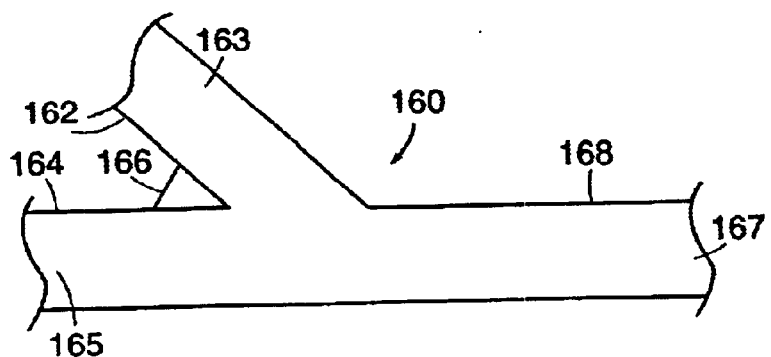
FIG. 8a shows a cross-sectional schematic view of a Y-shaped joint portion of a delivery catheter according to the invention.
Figure 8B:
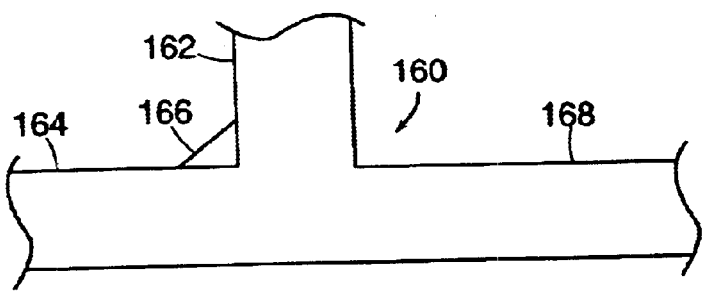
FIG. 8b shows a cross-sectional schematic view of a T-shaped joint portion of a delivery catheter according to the invention.

As shown in FIG. 2a, elongated members 100 and 200 are connected together by a joint 160 that permits access of at least a portion of the second elongated member 200 inside the lumen of the first elongated member 100. The joint 160 shown in FIGS. 8a–b includes extension legs 162, 164, and 168 and openings 163, 165, and 167. Openings 163 and 165 allow access of the lumen of the first elongated member by the second elongated member 200 and by the fluids flowing into the joint 160 from legs 162 and 164. Opening 167 allows connection of the joint 160 with the rest of the first elongated member 100 and fluid communication with the distal section 140. A bridge 166 can be included to secure or fortify the connection between the legs and the rest of the first elongated member 100. The joint 160 as depicted in FIG. 8a has a "Y" shape (with less than 90° angles between legs 162 and 164) while that in FIG. 8b has a "T" shape (with 90° angles between legs 162 and 164). Other shapes may also be adopted.

Referring again to FIG. 2a, the distal valve 210 of the delivery catheter 12 allows the second lumen 220 to be shut off upon release of pressure from the injector 180. A shut-off of the second lumen 220 results in termination of the feed of the crosslinkable polymer into the distal section 140. No further crosslinking of the polymer occurs upon the termination of the feed of the polymerizable agent into the distal section 140. Diffusion of the crosslinking agent is completely prevented from entering the second lumen 220 when the distal valve 210 is closed.

Figure 9A:
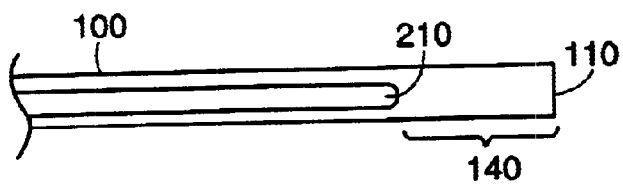
FIG. 9a shows a partial cross-sectional schematic view, illustrating one possible position of the second elongated member within the lumen of the first elongated member.
Figure 9B:
FIG. 9b shows a partial cross-sectional schematic view, illustrating one possible position of the second elongated member within the lumen of the first elongated member.
Figure 9C:
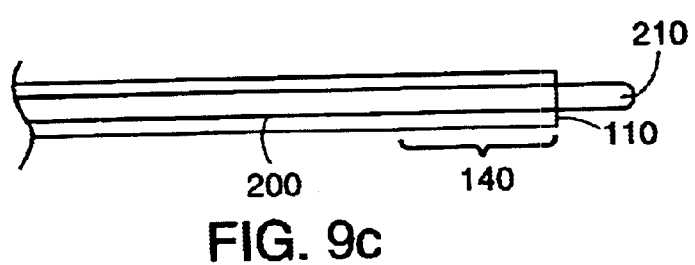
FIG. 9c shows a partial cross-sectional schematic view, illustrating one possible position of the second elongated member within the lumen of the first elongated member.

The delivery catheter of the invention allows at least a portion of the second elongated member to be slidable within the first lumen 120 of the first elongated member 100. To release the crosslinked polymeric material formed in and concomitantly to rid it from the distal section 140, the second elongated member 200 with the distal valve 210 closed can be pushed forward towards the distal end 110 of the first elongated member 100. The pushing and sliding of the distal valve 210 may cover as much as the full length of the distal section 140 or more to assist in clearing the distal section 140 of any formed crosslinked polymer such as alginate fibers. The distal valve 210 together with the second elongated member 200 can subsequently be retracted to its original setting to resume fiber delivery. Maintenance of pressure and fluid flow in the first lumen 110 can also facilitate removal of the crosslinked polymer from the distal section 140 by flushing the fiber out of the distal section 140. FIGS. 9a–c illustrate as a cartoon the sliding motion of elongated member 200 within elongated member 100. FIG. 9a shows the second elongated member 200 with the distal valve 210 positioned proximally to the distal section 140 and the distal opening 110 of the first elongated member 100. FIG. 9b shows the second elongated member 200 with the distal valve 210 positioned distally to the distal section 140 and near or at the distal opening 110 of the first elongated member 100. FIG. 9c shows the second elongated member 200 with the distal valve 210 positioned distally to the distal section 140 and distal to the distal opening 110 of the first elongated member 100.

The injectors 180 and 280 allow introduction of the crosslinkable polymeric material and the crosslinking agent into the first and second lumens. Syringes 180 and 280 may also provide pressure in the corresponding lumen to facilitate removal of the fiber from the distal section 140. Depending on the application, any type of injector may be employed if the desired delivery can be effectively conducted and the desired pressure exerted.

The delivery catheter may include, instead of or in addition to syringes or injectors, one or more automated pumps. For example, in the delivery system 16 shown in FIG. 10a, a first pump 183 may be connected to and in fluid communication with the first elongated member 100 and the first lumen 120 through connection port or seal 170 and joint 160. A second pump 283 may be connected to and in fluid communication with the second elongated member 200 and lumen 220 through connection port or seal 270 of joint 160. Similar to pressure control through injectors, the pressure and material flow in the first and the second lumens 120 and 220 may be controlled by the pumps 183 and 283. Reservoirs 196 and 296 are connected to pumps 183 and 283 respectively to supply the first and second materials to the lumens 120 and 220 of elongated members 100 and 200 (FIG. 10b), respectively. Any types of pumps may be used as long as the purpose of controlling pressure and effecting material delivery is achieved. A pump can be advantageously used with a typical syringe in effecting a continuous delivery. Such automated syringes or injectors are well known in the art. Automated and/or computerized control of the pressure and material flow may also be achieved through a control system 298 by incorporating appropriate computerized equipment and software.

Referring to FIGS. 11a–c, the delivery catheter can be incorporated into a gun-like handheld delivery system that allows easy control of delivery and termination of the polymeric fibers. In addition to features previously described in FIG. 2a, the gun-like delivery system 14 includes a handle 190, a trigger or releaser 192 disposed in a chamber 193, a panel 194 and a cover 195 for attaching injectors 180 and 280, and mechanisms for effecting an injection upon the pulling or release of the trigger or releaser 192. The trigger or releaser 192 mechanically controls the movement of injectors 180 and 280 through mechanisms (such as levers, gears, ratchet and pawl, and/or motors, not shown). These mechanisms are known and within the skill of the trained artisan.

In certain applications, the delivery catheter may include more than two elongated members to introduce simultaneously more than two separate agents or components into the distal section. Two embodiments of a delivery catheter with three elongated members are shown in FIGS. 12 and 13 where each of the delivery catheters 18 and 19 includes elongated members 300, 400, and 500 defining corresponding lumens 320, 420, and 520.

Figure 12:
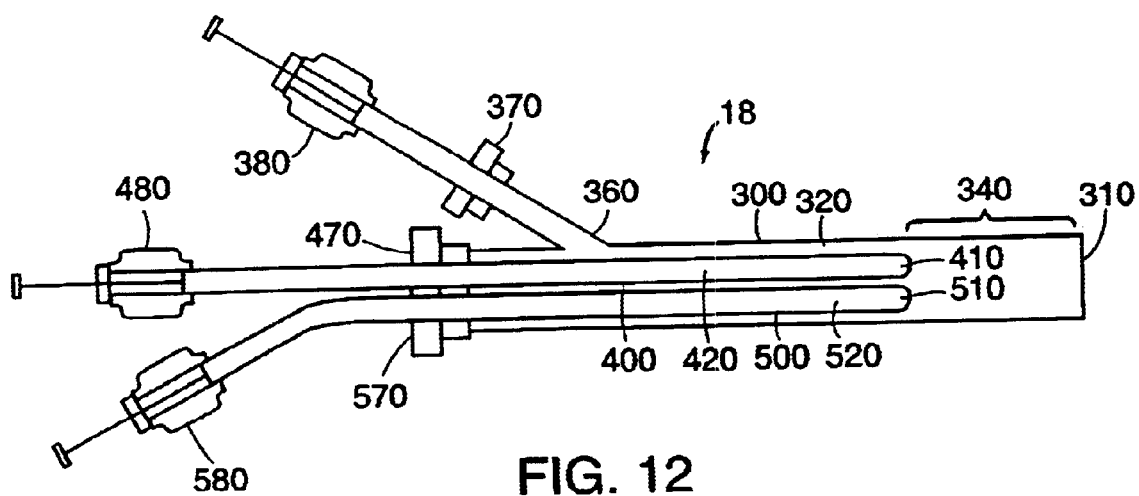
FIG. 12 is a partial cross-sectional schematic view of an embodiment of a delivery catheter according to the invention, illustrating the arrangement of an embodiment of a delivery system according to the invention including three elongated members (parallel/coaxial arrangement).

In FIG. 12, elongated members 400 and 500 are parallel and side-by-side while each is inside elongated member 300.

The remainder of the delivery catheter 18 is analogous to the delivering catheter shown in FIG. 2a including a distal section 340, distal valve 410 and/or distal valve 510, joint 360, connection ports or seals 370, 470, and 570, and injectors 380, 480, and 580. Elongated member 400 with distal valve 410 and/or elongated member 500 with distal valve 510 are slidable within the first lumen 320 to near or outside of distal opening 310. Thus, clearing of the distal section 340 can be accomplished by either or both slidable distal valves 410 and 510.

Figure 13:
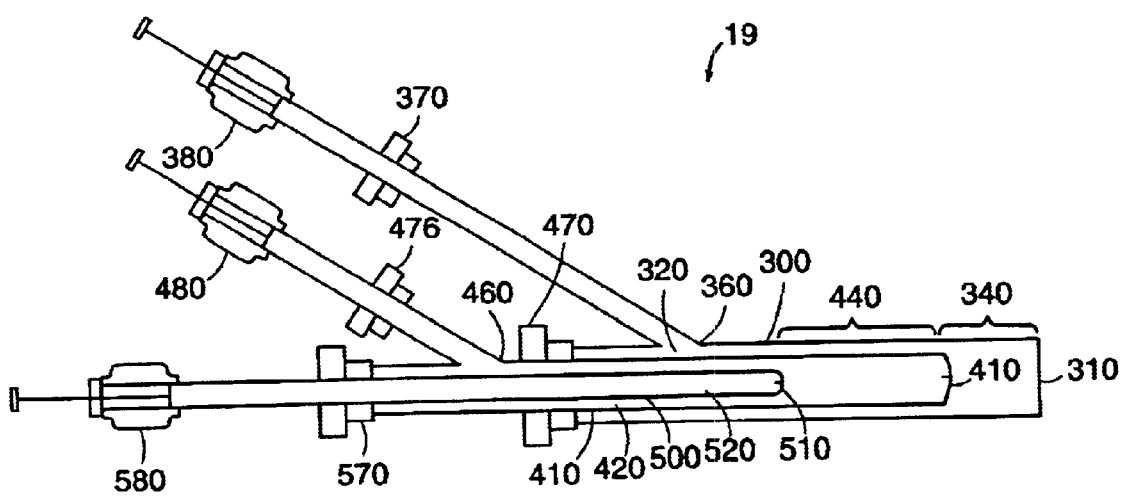
FIG. 13 is a partial cross-sectional schematic view of an embodiment of a delivery catheter according to the invention, illustrating the arrangement of an embodiment of a delivering system according to the invention including three elongated members (all-coaxial arrangement).

Referring to FIG. 13 in another embodiment, a first elongated member 500 is inside a second elongated member 400 that is in turn inside a third elongated member 300. The remainder of the delivery catheter 19 is analogous to the delivery catheter shown in FIG. 2a including lumens 320, 420, and 520, distal sections 340 and 440, distal valve 510 and/or distal valve 410, joints 360 and 460, connection ports or seals 370, 470, 476, and 570, and injectors 380, 480, and 580. Elongated member 400 with distal valve 410 is slidable within lumen 320 to near or outside of distal opening 310. Elongated member 500 with distal valve 510 is slidable within lumen 420 to near or outside of distal opening 410. Thus, clearing of the distal section 340 can be accomplished by sliding distal valves 410 with the elongated member 400. Clearing of the distal section 440 can be accomplished by sliding distal valves 510 with the elongated member 500.

Similarly, these or other additional elongated members may be employed for introduction of additional materials as necessitated by the application. For example, additional elongated members may be employed for introduction of other agents such as bioactive agents. Such bioactive agents include antibiotics, anti-inflammatory agents, antimicrobials, anti-infective agents, tissue growth promoters, anti-adhesion agents, and bioadhesives. While these materials may be mixed and introduced with either the crosslinking agent or the crosslinkable polymer, it may be advantageous to introduce them separately through additional elongated member(s) as described above. For example, the side-by-side arrangement may be well suited for co-delivering of a bioadhesive agent and a homeostatic agent to coat the fiber. The coaxial arrangement may be suited for encapsulation of a therapeutic agent within the fiber, such as an antibiotic agent.

Stabilizing structures (e.g., 250 in FIG. 2a) may be included in the delivery catheter to stabilize the elongated members. For example, the stabilizer may contain two or more legs peripherally placed between an annular wall of a distal segment of the first elongated member and an annular wall of a distal segment of the second and or additional elongated member. Stabilizing structures can be used to keep either the openings and/or the distal segments of the elongated members substantially co-axial or parallel to each other.

The devices and methods of the invention may be used to form polymeric fibers such as alginate fibers, or other forms of products, fibrous or nonfibrous.

Besides alginates, any crosslinkable polymers may be employed with a crosslinking agent using the devices and methods of the invention. Other crosslinkable polymers that may be suitable for use with the delivery catheter of the invention include both ionically crosslinkable and non-ionically crosslinkable polymers. To be used in conjunction with these crosslinkable polymers, crosslinking agents that may be employed include both ionic crosslinkers and non-ionic crosslinkers, respectfully.

The ionically crosslinkable polymeric material may be anionic or cationic and may include, but are not limited to, at least one polymer or copolymer such as polyacrylic acids, polymethacrylic acid, polyethylene amine, polysaccharides, alginic acid, pectinic acids, carboxy methyl cellulose, hyaluronic acid, heparin, chitosan, carboxymethyl chitosan, carboxymethyl starch, carboxymethyl dextran, heparin sulfate, chondroitin sulfate, cationic starch, and salts thereof. Illustrative examples of cationic crosslinking ions include polycations such as calcium, magnesium, barium, strontium, boron, beryllium, aluminium, iron, copper, cobalt, lead, and silver ions. Illustrative examples of anionic crosslinking ions include polyanions such as phosphate, citrate, borate, succinate, maleate, adipate and oxalate ions, and, more broadly, anions derived from polybasic organic or inorganic acids. The crosslinker can be a cation or an anion, either can be mono- or poly-charged ion. The preferred crosslinking cations are barium. The preferred crosslinking anions are phosphates.

Non-ionic crosslinking agents may be employed with non-ionically crosslinkable polymers. Non-ionic crosslinkers may also be used instead of or in addition to ionic crosslinkers with ionically crosslinkable polymer. Thus, a higher crosslinking density and improved mechanical properties, i.e., improved stiffness, modulus, yield stress and strength, may be accomplished by additionally subjecting the ionically crosslinkable polymer to non-ionic crosslinking. For example, non-ionic crosslinking can be accomplished by treatment with a chemical crosslinking agent which reacts with groups present in the polymer such that covalent bonds are formed connecting different portions of the polymer or between polymer strands to form a web.

Suitable non-ionic crosslinking agents are polyfunctional compounds preferably having at least two functional groups reactive with one or more functional groups present in the polymer. The crosslinking agent can contain one or more of carboxyl, hydroxy, epoxy, halogen, amino functional groups or hydrogen unsaturated groups. Illustrative non-ionic crosslinking agents include polycarboxylic acids or anhydrides, polyamines, epihalohydrins, diepoxides, dialdehydes, diols, carboxylic acid halides, ketenes and like compounds. Illustrative crosslinkable polymers include those that possess organic acid functional groups that are covalently crosslinkable with polyfunctional crosslinking agents. The covalent bonds between the crosslinking agents and the hydrophilic polymers are susceptible to hydrolysis in the body, releasing water-soluble components.

One embodiment utilizes crosslinking agents that can form relatively weak covalent crosslinking bonds, so that these bonds can be de-crosslinked within the body after a desired length of time. For example, polymers comprising covalent bonds that are easily hydrolysable at temperature and pH conditions inside the body can serve this purpose. Such polyfunctional covalent crosslinking agents include polyfunctional aziridines, polyfunctional carbodiimides, polyisocyanate, glutaraldehyde or other polyfunctional crosslinkers wherein the ftnctional groups are capable of reacting with the organic acid groups, or any activated forms thereof.

Alginate is an inonically crosslinkable polymer. Alginate is a heterogeneous group of linear binary co-polymer of 1–4 linked βD-mannuronic acid (M) and its C-5 epimer O-L-guluronic acid (G). The monomers are arranged in blockwise pattern along the polymer chain where mannuronic blocks (M blocks) and guluronic blocks (G blocks) are interspaced with sequences containing both M monomers and G monomers (mixed or MG blocks). The proportion and sequential arrangement of the uronic acids in alginate depend upon the species of algae and the kind of algal tissue from which the material is prepared. Commercial alginates are produced from sources including *Laminaria hyperborea, Macrocystis pyrifera, Laminaria digitata, Ascophyllum nodosum, Laminariajaponica, Eclonia maxima, Lesonia negrescens and Saragassum sp.*

Monovalent cation alginate salts, such as sodium or potassium alginate, are water soluble. Most divalent cations, such as calcium, strontium, or barium, interact with alginate to form water insoluble but water permeable gels. Because of the higher affinity of these divalent cations for guluronate compared with mannuronate blocks and because of steric considerations, cooperative binding of gelling divalent cations to guluronate within guluronate blocks provides the primary intermolecular crosslinking responsible for formation of stable alginate gels. Mannuronate and mixed blocks are not crosslinked due to their weaker affinity for the crosslinking divalent cation, but function as flexible interconnecting segments between interacted guluronate blocks.

Different divalent cations have different affinities for mannuronate and guluronate and thus are differentially susceptible to be displaced by exchange with other monovalent or divalent cations. Likewise, depending on the molecular weight, the number of residues per block and the overall ratio of guluronate to mixed or mannuronate blocks, different alginates have different susceptibilities to undergo ion exchange reactions.

The degree of crosslinking, both ionic and non-ionic, can be controlled mainly as a function of the concentration of the crosslinking agent. The crosslinking agent may be in a solution of water or of another suitable solvent or mixture thereof. The solvent is not limited as long as it is suitable for the application. In solution, the concentration of the crosslinking agent can range from about 0.0001 M to about 10 M and is to be determined according to the application. In one embodiment, the concentration of the crosslinking agent ranges from about 0.0001 M to about 0.001 M. In another embodiment, the concentration of the crosslinking agent ranges from about 0.001 M to about 0.01 M. In yet another embodiment, the concentration of the crosslinking agent ranges from about 0.01 M to about 0.1 M. In yet another embodiment, the concentration of the crosslinking agent ranges from about 0.1 M to about 1.0 M. In yet another embodiment, the concentration of the crosslinking agent ranges from about 1.0 M to about 10 M.

Similarly, the crosslinkable polymer such as alginate may be in a solution of water or any solvent suitable for the application. In solution, the concentration of the crosslinkable polymer can range from about 0.0001 M to about 10 M and is to be determined according to the application. In one embodiment, the concentration of the crosslinkable polymer ranges from about 0.0001 M to about 0.001 M. In another embodiment, the concentration of the crosslinkable polymer ranges from about 0.001 M to about 0.01 M. In yet another embodiment, the concentration of the crosslinkable polymer ranges from about 0.01 M to about 0.1 M. In yet another embodiment, the concentration of the crosslinkable polymer ranges from about 0.1 M to about 1.0 M. In yet another embodiment, the concentration of the crosslinkable polymer ranges from about 1.0 M to about 10 M.

Various additives may be added in the solution of the crosslinking agent, the solution of alginate, or both. For example, a bioadhesive agent may be added to the solution of the crosslinking agent and/or the solution of alginate. Illustrative bioadhesive agents include, but are not limited to, collagen, laminin, fibronectin, poly-D-lysine, poly-L-lysine, decapeptides. Also, materials that enhance the radiopacity of the fiber may be added to the solution of the crosslinking agent, the solution of alginate, or both. Illustrative examples of radiopaque agents in liquid or solid form include, but are not limited to, tantalum powder, platinum powder, barium sulfate, bismuth subcarbonate, ionic or non-ionic contrasting agents such as diatrizoates, iodipamide, iohexol, iopamidol, iothalamate, ioversol, ioxaglate, and metrizamide. Examples of liquid contrasting agents include Omnipaque®, Visipaque® manufactured by Nycomed Amersham Imaging of Princeton, New Jersey, or RenoCal® manufactured by Bracco Diagnostic Inc. of Princeton, N.J. Other natural or synthetic additives that may be added include, but are not limited to, anti-inflammatory agents, antimicrobials such as antibiotics or antifungal agents, anti-viral agents, anti-infective agents, tissue growth promoters, immunosuppressants, and anti-adhesion agents.

In another aspect, the invention relates to methods for delivering an extrudable material within the body of a mammal. In one embodiment, the method includes the following steps. A delivery catheter as described above is provided to deliver a first and second materials into a body. A fibrous material is extruded out of the distal section and into the body of a mammal. In one embodiment, the extrusion step includes delivering through the first lumen to the distal section a first material having a crosslinking agent and delivering through the second lumen to the distal section a second material having a crosslinkable polymer.

To deliver a fiber into the body of a mammal, the distal segment of a delivery catheter is inserted into a body of a patient either percutaneously or by entry into an existing orifice or duct. Access into the body may be direct or with the help of trocars, stylets, needles, cannulas, dilators, endoscopes or the like. A first material containing a crosslinking agent and a second material containing a crosslinkable polymer are introduced into the distal section through the first lumen and the second lumen, respectively.

In one embodiment of the invention, as the first material and the second material are introduced into the mixing chamber, the first material surrounds the second material. The contacting of the first and the second materials results in the formation of crosslinked polymeric material inside the distal section and formation of a fibrous structure. The sustained delivering of the first and second materials to the distal section creates a continuously growing fiber of crosslinked polymeric material. The formation of the fiber may be terminated by terminating the feed of either or both the first and second materials. The method may further include a step of cutting the fiber so formed. The fiber may be cut by the termination of the feed of one or both of the first and second materials into the distal section, or additionally, by an action of the valve walls which operate as blades and the closing of which operates as a transversal slicing of the fiber.

To facilitate the exiting of the terminated fibers from the distal section, the fibers may be pushed out of the distal section by sliding distally the second elongated member and/or by maintaining pressure or flow of the crosslinking agent solution in the first lumen. The delivery catheter allows the second elongated member to penetrate into the distal section thereby pushing the formed fibers out of the distal section. Thereafter, the formation and termination process can be repeated as needed by repeating the sequence of steps described herein above.

Figure 14A:
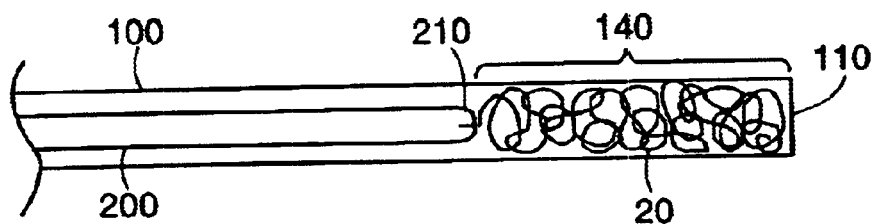
FIG. 14a shows formation of fibrous material within a delivering catheter according to the invention.
Figure 14B:
FIG. 14b shows removal of fibrous material from a delivery catheter according to the invention.

Referring to FIGS. 14*a*–*b*, fibers 20 such as alginate fibers are formed inside the distal section 140 as the crosslinking agent and the alginate solution are introduced into the distal section 140 through the first lumen 120 and the second lumen 220, respectively. The distal section 210 and the second elongated member 200 can be slid toward the distal opening 110 (FIG. 14b). Such sliding results in alginate fibers 20 being pushed out of the distal section 140. Referring to FIGS. 9a–c again, the second lumen 200 with the distal valve 210 can be slid to a position such that the distal valve 210 is distal to the distal opening 110.

In one embodiment of the invention, the first material is a solution containing a crosslinking agent. The second material is a solution containing a crosslinkable polymer. As the crosslinking agent and the alginate enter the distal section, the crosslinking agent solution surrounds the crosslinkable polymer solution. In another embodiment, the first material is a solution containing a crosslinkable polymer. The second material is a solution containing a crosslinking agent. As the crosslinking agent and the crosslinkable polymer enter the distal section, the crosslinkable polymer solution surrounds the crosslinking agent solution.

The devices and methods of the present invention may be used for any treatment, including urological and neurological procedures, involving the introduction of a filler into the body by mixing two or more agents in the body of a mammal. In certain applications, the crosslinked polymeric material may be formed and used outside the body of a mammal.

EXAMPLE 1

A solution (Solution 1) of a crosslinking agent (calcium chloride, 0.5 wt. % to 5.0 wt. %) and a bioadhesive agent (polyethylene oxide, 0.5 wt. % to 5.0 wt. %) is placed in a syringe (Syringe 1). A solution (Solution 2) of a commercially available alginate (sold by Pronova of Oslo, Sweden, sodium alginate, 0.5 wt. % to 5.0 wt. %) is placed in a second syringe (Syringe 2). The concentrations of the reagents in Syringes 1 and 2 may be varied to increase or decrease the crosslinking rate of the alginate. Syringes 1 and 2 are then connected to the "Y" shaped joint of the fiber delivery catheter. Solutions 1 and 2 are then injected into the distal section of the first lumen wherein an alginate fiber forms at a rate that depends on the concentrations of solution 1 and 2. A typical rate of fiber formation may be 0.2 mL/min. This rate can be varied with changing the crosslinking agent to alginate ratio. The rate of crosslinking is also affected by the use of additives such as radiopaque fillers as well as other additives such as listed above in The pressure from Syringe 2 is released, resulting in the closing of the distal valve and the termination of the delivery of Solution 2 into the distal section. At the same time, the closing of the distal valve cuts the alginate fiber already formed. Pushing of the second elongated member by pushing Syringe 2 forwards removes the alginate fiber out of the distal section. Syringe 2 is then withdrawn back to its original location and alginate fiber formation can be resumed by actuation of the plungers in Syringes 1 and 2, opening the distal valve, and injection of Solutions 1 and 2 into the distal section.

Variations, modifications, and other implementations of what is described herein will occur to those of ordinary skill without departing from the spirit and the scope of the invention. Accordingly, the invention is not to be defined or limited only by the preceding illustrative description.

What is claimed is:
1. A delivery catheter, comprising:
  (a) a first elongated member defining a first distal opening and a first lumen extending within the first elongated member, the first elongated member for delivering a first material through the first lumen and into a distal section of the first lumen near the first distal opening;
  (b) a second elongated member comprising a distal valve and a second lumen extending within the second elongated member, the second elongated member for delivering a second material through the second lumen and the distal valve, at least a portion of the second elongated member being slidably disposed within at least a portion of the first lumen such that the distal valve is selectively slidable
    (i) to allow delivery of the second material through the second lumen and the distal valve and into the distal section, and
    (iv) to push at least some of the first and second materials from the distal section and out of the first distal opening;
  (c) a first injector adapted for connection to the first elongated member for injecting the first material into the first lumen; and
  (d) a second injector adapted for connection to the second elongated member for injecting the second material into the second lumen.

2. The catheter of claim 1 wherein the distal valve comprises a one-way flow-control valve.

3. The catheter of claim 2 wherein the one-way flow-control valve comprises a slit that opens and closes upon pressure differentiation between the second lumen and the distal section to regulate delivery of the second material into the distal section.

4. The catheter of claim 3 wherein the slit opens to a size of about 0.00001 mm$^2$ to about 100 mm$^2$.

5. The catheter of claim 1 wherein one of the first and second lumens has a diameter of about 0.001 mm to about 20 mm.

6. The catheter of claim 1
  wherein said first injector comprises a first pump connected to the first elongated member for delivering the first material into the first lumen; and
  wherein said second injector comprises a second pump connected to the second elongated member for delivering the second material into the second lumen.

7. The catheter of claim 6 wherein each of the first and second pumps comprises a syringe.

8. The catheter of claim 1 wherein the first elongated member further defines a first proximal port, and the second elongated member further defines a second proximal port.

9. The catheter of claim 8 further comprising an access joint between a first proximal joint and the first distal opening, the access joint allowing insertion of the at least a portion of the second elongated member into the at least a portion of the first lumen.

10. The catheter of claim 9 wherein the access joint is Y-shaped.

11. The catheter of claim 9 wherein the access joint is T-shaped.

12. The catheter of claim 1 further comprising a stabilizer to keep the second elongated member substantially co-axial with the first elongated member.

13. The catheter of claim 12 wherein the stabilizer comprises two or more legs peripherally placed between an annular wall of a distal segment of the first elongated member and an annular wall of a distal segment of the second elongated member.

14. The catheter of claim 1 wherein the selectively slidable distal valve is alternatively positionable outside the first lumen and outside the first distal opening.

15. The catheter of claim 1 wherein at least one of the first and second elongated members has a length from about 1 cm to 3 m.

16. A delivery catheter, comprising:
(a) a first elongated member defining a first distal opening and a first lumen extending within the first elongated member, the first elongated member for delivering a first material through the first lumen and into a distal section of the first lumen near the first distal opening;
(b) a second elongated member comprising a distal valve and a second lumen extending within the second elongated member, the second elongated member for delivering a second material through the second lumen and the distal valve, at least a portion of the second elongated member being slidably disposed within at least a portion of the first lumen such that the distal valve is selectively slidable
  (i) to allow delivery of the second material through the second lumen and the distal valve and into the distal section, and
  (ii) to push at least some of the first and second materials from the distal section and out of the first distal opening;
(c) a first pump connected to the first elongated member for delivering the first material into the first lumen; and
(d) a second pump connected to the second elongated member for delivering the second material into the second lumen.

17. The catheter of claim 16 wherein each of the first and second pumps comprises a syringe.

18. A delivery catheter, comprising:
(a) a first elongated member defining a first distal opening, a first proximal port and a first lumen extending within the first elongated member, the first elongated member for delivering a first material through the first lumen and into a distal section of the first lumen near the first distal opening;
(b) a second elongated member comprising a distal vave and a second lumen extending within the second elongated member, the second elongated member defining a second proximal port and for delivering a second material through the second lumen and the distal valve, at least a portion of the second elongated member being slidably disposed within at least a portion of the first lumen such that the distal valve is selectively slidable
  (i) to allow delivery of the second material through the second lumen and the distal valve and into the distal section, and
  (ii) to push at least some of the first and second materials from the distal section and out of the first distal opening; and
(c) an access joint between a first proximal joint and the first distal opening, the access joint allowing insertion of the at least a portion of the second elongated member into the at least a portion of the first lumen.

19. The catheter of claim 18 wherein the access joint is Y-shaped.

20. The catheter of claim 18 wherein the access joint is T-shaped.

21. A delivery catheter, comprising:
(a) a first elongated member defining a first distal opening, a first proximal port and a first lumen extending within the first elongated member, the first elongated member for delivering a first material through the first lumen and into a distal section of the first lumen near the first distal opening;
(b) a second elongated member comprising a distal valve and a second lumen extending within the second elongated member, the second elongated member defining a second proximal port and for delivering a second material through the second lumen and the distal valve, at least a portion of the second elongated member being slidably disposed within at least a portion of the first lumen such that the distal valve is selectively slidable
  (i) to allow delivery of the second material through the second lumen and the distal valve and into the distal section, and
  (ii) to push at least some of the first and second materials from the distal section and out of the first distal opening; and
(c) a stabilizer to keep the second elongated member substantially co-axial with the first elongated member.

22. The catheter of claim 21 wherein the stabilizer comprises two or more legs peripherally placed between an annular wall of a distal segment of the first elongated member and an annular wall of a distal segment of the second elongated member.

* * * * *

UNITED STATES PATENT AND TRADEMARK OFFICE
CERTIFICATE OF CORRECTION

| | | |
|---|---|---|
| PATENT NO. | : 6,663,596 B2 | Page 1 of 1 |
| APPLICATION NO. | : 09/928779 | |
| DATED | : December 16, 2003 | |
| INVENTOR(S) | : John A. Griego et al. | |

It is certified that error appears in the above-identified patent and that said Letters Patent is hereby corrected as shown below:

Col. 2, line 16, after first word "and", change "second pumps" to --a second pump--.

Col. 2, line 19, after "e.g.", insert --,--.

Col. 5, line 48, after "two-way", change "flow control" to --flow-control--.

Col. 6, line 10, after "(FIGS. 4*c-d*)", insert --,--.

Col. 6, line 11, after "valve", insert --210--.

Col. 6, line 25, after "that", change "opens" to --open--.

Col. 7, line 18, after "elevated", insert --,--.

Col. 10, line 3, after "acids,", change "carboxy methyl" to --carboxymethyl--.

Col. 12, line 21, after "and", change "second materials" to --a second material--.

Col. 13, line 42, after "of", change last word "solution" to --Solution--.

Col. 13, line 46, after "listed", change "above in" to --above.--.

Col. 13, line 52, after "Syringe 2", change "forwards" to --forward--.

Signed and Sealed this

Sixteenth Day of September, 2008

JON W. DUDAS
*Director of the United States Patent and Trademark Office*